United States Patent [19]
Dunham

[11] Patent Number: 6,080,108
[45] Date of Patent: Jun. 27, 2000

[54] SCANNING AID FOR QUANTIFIED THREE DIMENSIONAL ULTRASONIC DIAGNOSTIC IMAGING

[75] Inventor: Paul T. Dunham, Everett, Wash.

[73] Assignee: ATL Ultrasound, Inc., Bothell, Wash.

[21] Appl. No.: 09/193,657

[22] Filed: Nov. 17, 1998

[51] Int. Cl.$^7$ ...................................................... A61B 8/00
[52] U.S. Cl. .......................................................... 600/459
[58] Field of Search .................................... 600/456, 459, 600/460, 458, 45

[56] References Cited

U.S. PATENT DOCUMENTS

| | | |
|---|---|---|
| 3,741,004 | 6/1973 | Posakony . |
| 4,120,291 | 10/1978 | Paton et al. . |
| 4,341,120 | 7/1982 | Anderson . |
| 4,601,292 | 7/1986 | Fidel et al. ............................... 600/453 |
| 5,152,294 | 10/1992 | Mochizuki et al. ..................... 600/459 |
| 5,159,931 | 11/1992 | Pini . |
| 5,181,514 | 1/1993 | Solomon et al. . |
| 5,474,073 | 12/1995 | Schwartz . |
| 5,487,388 | 1/1996 | Rello et al. . |
| 5,562,095 | 10/1996 | Downey et al. . |
| 5,598,845 | 2/1997 | Chandraratna et al. ................ 600/459 |
| 5,671,746 | 9/1997 | Dreschel et al. ......................... 600/453 |

*Primary Examiner*—Marvin M. Lateef
*Assistant Examiner*—Maulin Patel
*Attorney, Agent, or Firm*—W. Brinton Yorks, Jr.

[57] ABSTRACT

A scanning aid is provided for aiding the user in obtaining 3D image data of a patient for rendering in a quantified 3D ultrasonic image. The scanning aid of the present invention relates the location of each piece of image data in three dimensional space to the physiology of the patient by relating the scanhead and its image planes to the patient. The scanning aid of the present invention provides the user with the ability to manually control the movement of the scanhead; the ability to obtain uniformly angularly spaced image planes regardless of the speed or variance in the motion of the scanhead; and the ability to obtain a repeatably fixed relationship between the scanhead and the scanning aid to assure the spatial precision of the acquired image data and to aid the user in repeatedly obtaining the same three dimensional ultrasonic images.

22 Claims, 3 Drawing Sheets

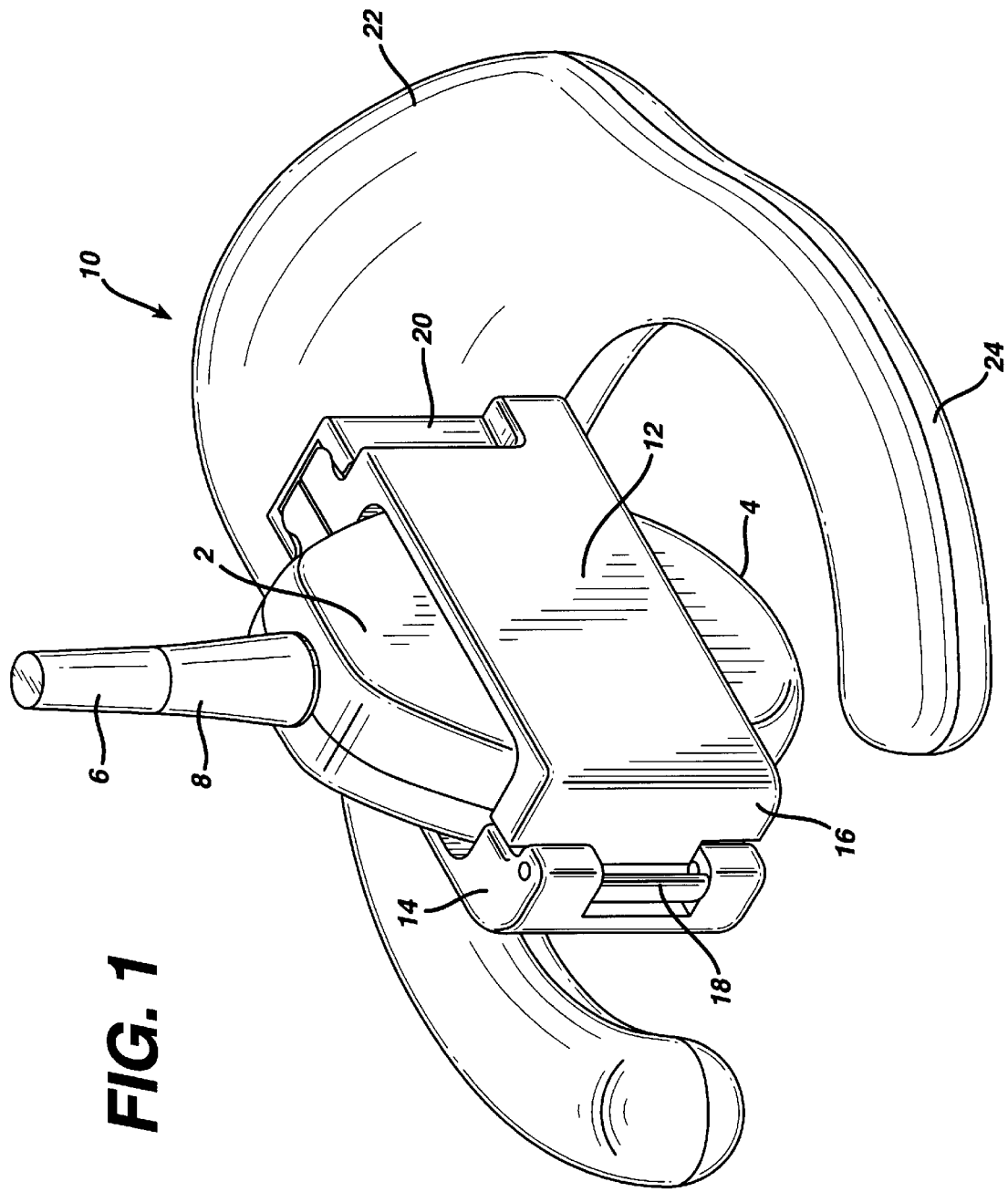

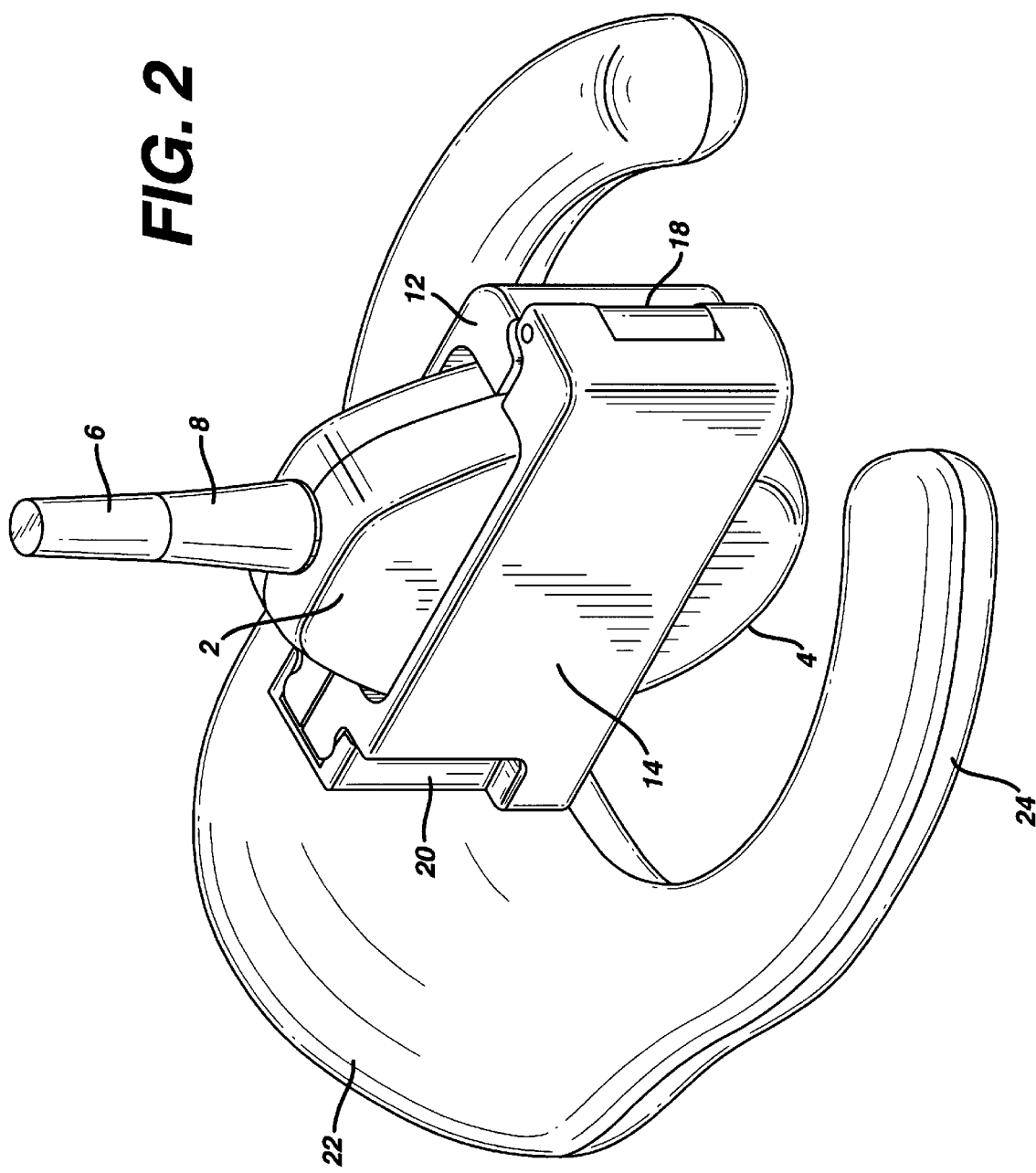

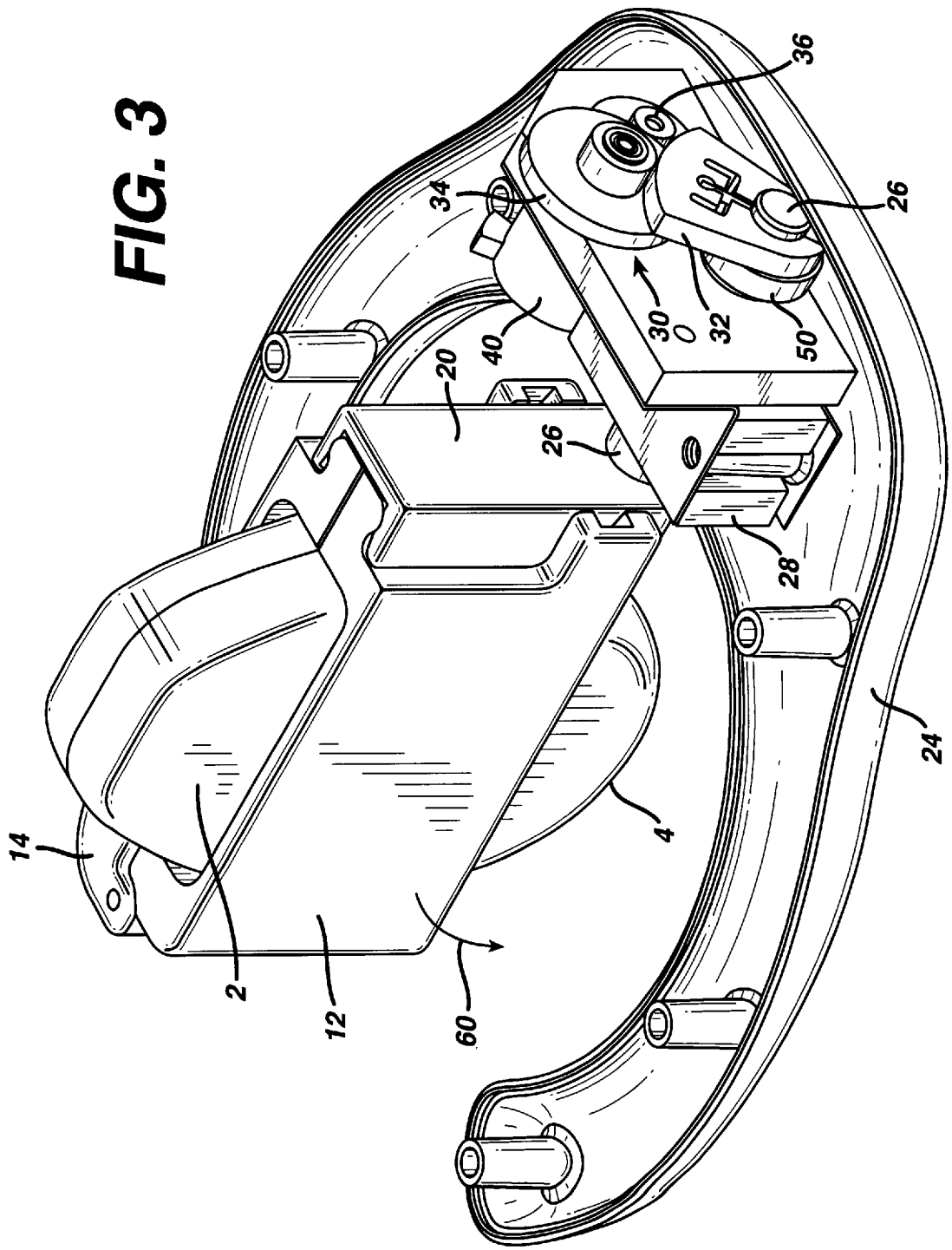

SCANNING AID FOR QUANTIFIED THREE DIMENSIONAL ULTRASONIC DIAGNOSTIC IMAGING

The present invention relates to scanning aids by which a medical ultrasound diagnostician can gather 3D image data of a patient for rendering in a quantified 3D ultrasonic image. By "quantified", it is meant that the location of each piece of image data in three dimensional space is known in relation to the physiology of the patient. This enables quantified use of the 3D ultrasound image, such as performing measurements of distances, diameters, and the like.

Ultrasonic diagnostic imaging systems are in widespread use for performing ultrasonic imaging and measurements of the human body. The internal structure of a body is viewed with the use of a scanning device such as a scanhead. The scanhead houses an array of transducer elements that transmits ultrasonic waves and receives ultrasonic echoes as the waves are reflected from internal structures of the body. As the ultrasonic waves are transmitted into the body an image or scan plane is created from received echoes, which is essentially the field of view of the scanhead.

Three dimensional images may be obtained by scanning individual points in a volumetric region of the body, or by sequencing a plurality of spatially related image planes, which are obtained by taking different slice planes of the volumetric region of a body being examined. The ultrasonic information obtained from spatially related image planes may be analyzed and displayed on the basis of spatial coordinates of the data within a plane, and on the basis of the spatial relationship of each plane to the others. Uniformly distributed image plane data can be used to render a three dimensional ultrasonic image as described in U.S. Pat. No. 5,474,073 or patent application Ser. No. 08/756,853 which is anatomically accurate and thus useful for quantified measurement.

Various scanning aids have been used for acquiring spatially related image planes. Such techniques include the use of devices that control the movement of the scanhead. For example, in U.S. Pat. No. 5,487,388, a three dimensional scanning technique is disclosed that uses motors to electromechanically drive the scanhead through its scanning motion. As the scanhead travels through the motion, a number of spatially related scan plane images are obtained in incremental intervals.

Scan plane images acquired with such a device are spatially related to an apex just below or above the skin of the patient. Thus, if the patient moves during the scanning process, any three dimensional images created from the obtained image planes may be anatomically inaccurate and thus not useful for quantified measurement. Users of such devices have less control over the speed and action of the scanhead motion as compared to techniques that allow the user to manually move the scanhead. While manual movement of the scanhead provides the user with greater control, it is difficult for the user to repeatedly obtain the same three dimensional ultrasonic images. It is also difficult for the user to maintain the motion of the scanhead at a constant speed such that the intervals of the image planes are evenly spaced for obtaining precise spatial image data.

Other scanning aids have been devised which reference a scanhead and its image data to the ultrasound machine or coordinates of the room in which scanning is performed. These include articulated arm devices and scanhead-mounted transmitter arrangements. Similar to the motorized device above, movement of the patient during the scanning process may cause any related images to be anatomically inaccurate and thus not useful for quantified measurement.

Accordingly, it is desirable to have a scanning aid that aids the user in obtaining 3D image data of a patient for rendering in a quantified 3D ultrasonic image. Such a scanning aid must be able to relate the location of each piece of image data in three dimensional space to the physiology of the patient.

In accordance with the principles of the present invention, a scanning aid is provided that relates the scanhead and its image planes to the patient. The scanning aid of the present invention provides the user with the ability to manually control the movement of the scanhead; the ability to obtain uniformly angularly spaced image planes regardless of the speed or variance in the motion of the scanhead; and the ability to obtain a repeatably fixed relationship between the scanhead and the scanning aid to assure the spatial precision of the acquired image data and to aid the user in repeatedly obtaining the same three dimensional ultrasonic images.

In the drawings:

FIG. 1 illustrates the scanning aid of the present invention;

FIG. 2 illustrates the scanning aid of the present invention from a different perspective; and FIG. 3 illustrates the internal mechanics of the scanning aid of the present invention.

Referring first to FIGS. 1 and 2, scanning aid 10 of the present invention is shown, which is used to scan with an ultrasonic probe or scanhead 2. The scanhead 2 is of conventional design and operation. The illustrated scanhead 2 is a curved array scanhead, which transmits ultrasonic waves and receives ultrasonic echoes through an acoustic window 4 which, in FIG. 1, is oriented downward. Extending from the top of the scanhead 2 is a cable 6 and strain relief 8. Other types of scanheads such as linear and phased array probes may also be used with the aid of the present invention.

The scanhead 2 is securely held in a clamp 12 which is comprised of two halves 14 and 16, which are hinged at one end 18. The closed clamp 12 is located in an upright mount 20, which securely retains the clamped scanhead 2 in the clamp 12. The main body of scanning aid 10 comprises an enclosure of smoothly rounded plastic formed from an upper half 22 and a lower half 24. The enclosure is formed as a gently curved body surrounding a central opening through which the scanhead 2 engages the body of a patient.

Turning now to FIG. 3, scanning aid 10 is shown with the upper half 22 of the enclosure removed. Mount 20 is shown connected to the main body of the scanning aid by a rotating shaft 26. Shaft 26 is retained in position by a plate 28 and bushing 50, which allow the shaft to rotate. Mounted on the end of the shaft is a sector gear 32 of a gear train 30. The gear train includes the sector gear 32 which engages an idler gear 34, which in turn engages a pinion gear 36. The pinion gear 36 is mounted on the end of the shaft of potentiometer 40. The resistive elements of the potentiometer are connected to electrical wires (not shown) which exit through a hole in the enclosure and connect to the ultrasound system which operates the scanhead 2.

The clamp 12 is keyed to lock repeatably into the same position in mount 20, and the inner surface of clamp 12 is likewise contoured or keyed to engage scanhead 2 in the same position in clamp 12 each time the scanhead is clamped in place. This provides a fixed orientation between the scanhead and the shaft 26 each time the scanhead is clamped into scanning aid 10. This repeatably fixed relationship of the scanhead and scanning aid assures the spatial precision of the acquired image data and that the same three dimensional ultrasonic images can be repeatedly acquired.

In use, the user places the scanning aid with its clamped scanhead on the body of a patient, over a region of the body where it is desired to acquire 3D ultrasonic images. The scanning aid thus references the scanhead to the body, and will move with the patient as the patient turns or breathes. The acoustic window 4 of the scanhead contacts the skin of the patient's body and is acoustically coupled to the body of the patient by an ultrasonic couplant (not shown).

To acquire three dimensional ultrasonic image data, the user grasps the clamped scanhead and rocks the scanhead from side to side as indicated by arrow 60. As the scanhead is manually rocked, the shaft 26 rotates and drives the gear train 30 which turns the shaft of potentiometer 40. The potentiometer will thereby produce an impedance which is proportional to the angular orientation of the scanhead to the body. When energized, the potentiometer will produce an output signal proportional to the angular orientation of the scanhead, and hence the angular orientation of the scan plane which the scanhead is scanning at each moment as it is rocked.

It is seen that the output signal of the scanning aid potentiometer can serve as a trigger signal for the scanhead, whereby image plane data can be acquired at uniformly angularly spaced increments as the scanhead is rocked in the scanning aid. The potentiometer output signal may be digitized and the digital signal used as the trigger signal for the scanhead's transmit beamformer. Each time the trigger signal changes by a predetermined amount, the scanhead is triggered to scan and acquire image data from its instantaneous image plane. As the scanhead is rocked from one end of its range of motion to the other, a sequence of angularly spaced image plane data is acquired. With proper linearity tolerances for the potentiometer, the acquired scanhead data will be uniformly angularly spaced in the plane to plane direction.

The scanning aid of the present invention is manually rocked to scan at a speed dictated by the action of the user. If the scanhead is rocked slowly, the potentiometer output signal will change correspondingly slowly, and will trigger imaging at relatively widely spaced time intervals. If the scanhead is rocked more quickly, the trigger signals will be produced at more rapid time intervals. If the rocking of the scanhead is non-uniform, that is, varies in speed, the trigger signals will be produced in correspondence with the changing motion.

What is claimed is:

1. A scanning aid for obtaining quantified three dimensional ultrasonic diagnostic imaging data with a manually swept ultrasonic probe, comprising:
    a reference surface for referencing said probe with a body being examined by said probe;
    a holding device coupled to said reference surface for removably holding said probe in a predetermined position relative to said reference surface;
    a rotatable shaft coupled to said holding device for supporting movement of said probe as it is manually moved; and
    a position sensing device coupled to said rotatable shaft for sensing the position of said probe relative to said body as said probe is manually moved by a user to scan a volumetric region of said body.

2. The scanning aid of claim 1, wherein said position sensing device provides an electrical output signal electrically coupled to a medical diagnostic ultrasound system.

3. The scanning aid of claim 2, wherein said output signal is proportional to the angular orientation of said probe relative to said body.

4. The scanning aid of claim 3, wherein said output signal is coupled to said probe for triggering said probe with a trigger signal to instantaneously scan and acquire image data from a plurality of said probe's image plane positions.

5. The scanning aid of claim 4, wherein said trigger signal triggers said probe each time said trigger signal changes by a predetermined amount for acquiring a sequence of uniformly angularly spaced image plane data.

6. The scanning aid of claim 5, wherein said position sensing device is a potentiometer.

7. The scanning aid of claim 1, wherein said holding device is keyed to lock said probe in said holding device for holding said probe in a predetermined position relative to said rotatable shaft.

8. The scanning aid of claim 7, wherein said holding device is comprised of first and second opposing halves coupled together.

9. The scanning aid of claim 8, wherein said first and second opposing halves are hingedly coupled together.

10. A scanning aid for obtaining quantified three dimensional ultrasonic diagnostic imaging data with a manually swept ultrasonic probe, comprising:
    a reference surface for referencing said probe with a body being examined by said probe;
    a holding device coupled to said reference surface for removably holding said probe in a predetermined position relative to said reference surface;
    a rotatable shaft coupled to said holding device for supporting movement of said probe as it is manually moved; and
    a position sensing device coupled to said rotatable shaft for producing an electrical output signal electrically coupled to a medical diagnostic ultrasound system, wherein said output signal is proportional to the angular orientation of said probe relative to said body; and
    triggering means coupled to receive said output signal for triggering said probe proportionally to the speed of said probe movement to instantaneously scan and acquire image data from a plurality of said probe's image plane positions as said probe is manually moved by a user to scan a volumetric region of said body.

11. The scanning aid of claim 10, wherein said triggering means triggers said probe with a trigger signal each time said triggering means changes by a predetermined amount for acquiring a sequence of uniformly angularly spaced image plane data.

12. The scanning aid of claim 11, wherein said position sensing device is a potentiometer.

13. The scanning aid of claim 10, wherein said holding device is keyed to lock said probe in said holding device for repeatably holding said probe in a predetermined position relative to said rotatable shaft.

14. The scanning aid of claim 13, wherein said holding device is comprised of first and second opposing halves coupled together.

15. The scanning aid of claim 14, wherein said first and second opposing halves are hingedly coupled together.

16. A scanning aid for quantified three dimensional ultrasonic diagnostic imaging of a body with a manually swept ultrasonic probe, comprising:
    a reference surface;
    holding means coupled to said reference surface for removably holding said probe in a predetermined relationship with said reference surface;
    rotating means coupled to said holding means for supporting movement of said probe as it is manually moved;

positional sensing means coupled to said rotating means for sensing the position of said probe in relation to said body as said probe is manually moved by a user to scan said volumetric region; and data acquisition triggering means coupled to said positional sensing means for initiating said probe's acquisition of image data at intervals corresponding to the speed of said probe as said probe is manually moved by said user to scan a volumetric region of said body.

17. The scanning aid of claim 16, wherein said positional sensing means is comprised of a potentiometer electrically coupled to an ultrasonic diagnostic imaging system.

18. The scanning aid of claim 16, wherein said holding means is keyed to lock said probe in said holding means in a predetermined relationship to said rotating means for precisely and repeatedly acquiring image data.

19. The scanning aid of claim 18, wherein said holding means is comprised of first and second halves hingedly coupled together.

20. A scanning aid for quantified three dimensional ultrasonic diagnostic imaging of a body with a manually swept ultrasonic scanhead, comprising:

a reference surface;

holding means for removably coupling said scanhead to said reference surface in a predetermined relation to said body;

rotating means for supporting the manual movement of said scanhead in said holding means;

positional sensing means for sensing the angular orientation of said probe in relation to said body as said probe is manually moved by a user to scan a volumetric region of said body; and triggering means coupled to said positional sensing means for acquiring uniformly angularly spaced image plane data of said body by initiating said scan plane in intervals proportional to the speed of said scanhead as said scanhead is manually moved by said user.

21. A method of manually scanning a volumetric region of a body with an ultrasonic diagnostic imaging probe and a scanning aid comprising the steps of:

attaching said probe to said scanning aid in a predetermined position;

locating said scanning aid on the surface of said body;

manually moving said probe to scan said volumetric region;

receiving imaging trigger signals as said probe passes through predetermined scan plane orientations; and actuating said probe in response to said trigger signals, wherein the rate of said actuation is proportional to the speed of said probe movement.

22. The method of claim 21, wherein said actuating of said probe in response to said trigger signals is comprised of obtaining uniformly angularly spaced image plane data of said volumetric region.

* * * * *